United States Patent
Boger et al.

(10) Patent No.: US 7,115,660 B2
(45) Date of Patent: Oct. 3, 2006

(54) METHODS FOR INHIBITING ANGIOGENESIS AND TUMOR GROWTH

(75) Inventors: Dale L. Boger, La Jolla, CA (US); David A. Cheresh, Encinitas, CA (US)

(73) Assignee: The Scripps Research Institute, La Jolla, CA (US)

( * ) Notice: Subject to any disclaimer, the term of this patent is extended or adjusted under 35 U.S.C. 154(b) by 499 days.

(21) Appl. No.: 10/240,142

(22) PCT Filed: Mar. 27, 2001

(86) PCT No.: PCT/US01/09785

§ 371 (c)(1), (2), (4) Date: Sep. 27, 2002

(87) PCT Pub. No.: WO01/72297

PCT Pub. Date: Oct. 4, 2001

(65) Prior Publication Data

US 2003/0078296 A1    Apr. 24, 2003

(51) Int. Cl.
*A01N 47/10*    (2006.01)
*A61K 31/27*    (2006.01)
*A61K 31/21*    (2006.01)
*A61K 31/235*    (2006.01)
*A61K 31/16*    (2006.01)

(52) U.S. Cl. .................. 514/478; 514/483; 514/506; 514/532; 514/613; 514/617

(58) Field of Classification Search ................ 514/340, 514/478, 483, 506, 532, 613, 617
See application file for complete search history.

(56) References Cited

OTHER PUBLICATIONS

Kitoh et al, MMP2 and its activator membrane type 1-matrix metalloproteinase, J. Cell Sci., 109, 953-8, 1986.*

* cited by examiner

*Primary Examiner*—Alton Pryor
(74) *Attorney, Agent, or Firm*—Olson & Hierl, Ltd.

(57) ABSTRACT

Angiogenesis, tumor growth, and metalloproteinase 2 (MMP2) interaction with integrin-$\alpha_v\beta_3$ are inhibited by an inhibitor compound of formula (I): wherein $G^1$ and $G^2$ are each independently $NH-C(O)-O-R^1$, $-NH-C(O)-O-(CH_2)_v-(C_6H_4)-X^3$, $-NH-C(O)-NH-(CH_2)_v-(C_6H_4)-X^3$, $-O-C(O)-NH-(CH_2)_v-(C_6H_4)-X^3$, $-O-C(O)-O-(CH_2)_v-(C_6H_4)-X^3$, or $NH-C(O)-CH_2-(C_6H_4)-X^3$; $Y^1$ and $Y^2$ are each independently OH, $C_1-C_4$ alkyl, $C_1-C_4$ hydroxyalkyl, $C_1-C_4$ alkoxy, phenyl, benzyl, or $NH_2$; $R^1$ is $C_1-C_4$ alkyl; $X^1$ and $X^2$ are each independently halo or $C_1-C_4$ alkoxy; $X^3$ is halo, nitro, $C_1-C_4$ alkyl, $C_1-C_4$ alkoxy, or $C_1-C_4$ perfluoroalkyl; Z is $-C\equiv C-$, $-C_6H_4-$, cis-CH=CH—, trans CH=CH—, cis-$CH_2$—CH=CH—$CH_2$—, trans —$CH_2$—CH=CH—$CH_2$—, 1,4-naphthyl, cis-1,3-cyclohexyl, trans-1, 3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and p, r, and v are each independently an integer having a value of 1 or 2; with provisos that when A is H, t is 0; when A is a covalent bond, t is 1; when m is 0, $Y^1$ is $C_1-C_4$ hydroxyalkyl; and when n is 0, $Y^2$ is $C_1$ $C_4$ hydroxyalkyl.

2 Claims, 8 Drawing Sheets

1, A6B10

METHODS FOR INHIBITING ANGIOGENESIS AND TUMOR GROWTH

This invention was made with government support under Contract Nos. CA 78045, CA 45726, and CA 50286 by the National Institutes of Health. The United States Government has certain rights in this invention.

FIELD OF THE INVENTION

This invention relates to methods for inhibiting angiogenesis and tumor growth. More particularly, the invention relates to methods of inhibiting angiogenesis and tumor growth utilizing a compounds that selectively bind to integrin $\alpha_v\beta_3$ and blocks the interaction of integrin $\alpha_v\beta_3$ with matrix metalloproteinase 2 (MMP2).

BACKGROUND OF THE INVENTION

Invasion of vascular cells into tissues requires the coordinated interplay of numerous factors including proteinases, which remodel the extracellular matrix architecture, as well as cell adhesion molecules that recognize this provisional matrix. Recent reports have implicated that the 72 kDa matrix metalloproteinase 2 (MMP2) is a key player in vascular development and angiogenesis. For example, Kitoh et al. (*J. Cell Sci.*, 109, 953–8 (1996)) report that MMP2 and its activator membrane type 1-matrix metalloproteinase (MT1-MMP) are coordinately expressed by mesenchymal cells almost exclusively during embryonic development, indicating specific matrix remodeling constraints in these tissues. In addition, angiogenesis and corresponding tumor growth are reduced in MMP2 knockout mice (see Itoh et al., *Cancer Res.*, 58 1048–51 (1998)). Interestingly, Saftor et al. (*Proc. Natl. Acad. Sci. U.S.A.*, 89, 1557–61 (1992)) have shown that ligation of the integrin $\alpha_v\beta_3$, itself a known mediator of angiogenesis, induces MMP2 production, suggesting a coordinated interplay of these two molecules during the vascular remodeling associated with blood vessel formation (see also Bafetti et al., *J. Biol. Chem.*, 273, 143–9 (1998)). In fact, direct interaction between MMP2 and integrin $\alpha_v\beta_3$ has been demonstrated by Brooks et al. (*Cell*, 85, 683–93 (1996)). The negative regulation of MMP2 during vascular invasion and maturation was later shown by Brooks et al. to be dependent upon expression of $\alpha_v\beta_3$ (*Cell*, 92, 391–400 (1998)).

Although inhibition of angiogenesis and concomitant suppression of tumor growth by natural as well as synthetic inhibitors of MMP's, including MMP2, has been documented, the translation of such strategies into clinical modalities has met with limited success, primarily due to the deleterious side effects of such broad spectrum inhibitors. Since MMP function, in general, may be required for many processes in the adult organism, active site inhibition of enzymatic function is likely to have far reaching effects on various biological processes involving tissue remodeling, such as wound healing. In fact, it has been documented that therapies with broad spectrum MMP inhibitors in clinical studies of various cancer types cause severe side effects, including inflammatory tendinitis, polyarthritis, and muscoskeletal pain syndromes, which are dose limiting and often persist after discontinuation of therapy. Given the limited distribution of integrin $\alpha_v\beta_3$ in adult organisms, however, one would predict that targeting the interaction between MMP2 and $\alpha_v\beta_3$ to the areas of neovascularization or cellular invasion should correspondingly limit the effects of such treatment-related toxicities. Indeed, the recombinant non-catalytic carboxy-terminal hemopexin domain of MMP2 (PEX), which mediates MMP2 binding to integrin $\alpha_v\beta_3$ has shown antiangiogenic and antitumor activity in vivo. The potential utility of such a large protein fragment, but with attendant shortcomings (e.g. large scale production problems, FDA quality and safety control issues and antigenicity), suggested the need for a more practical solution to this problem.

There is a need therefore, for methods of inhibiting angiogenesis and tumor growth utilizing chemical compounds that selectively inhibit MMP activity at tumor growth sites with minimal inhibition of MMP in other regions of the body. There is also a need for methods of specifically binding to the MMP2 binding site of integrin $\alpha_v\beta_3$.

SUMMARY OF THE INVENTION

The present invention provides a method for the inhibition of the interaction of MMP2 with integrin $\alpha_v\beta_3$ and a method for inhibition of angiogenesis in cells containing integrin $\alpha_v\beta_3$. Further, the invention provides a method for inhibition of tumor growth by administration of MMP2-$\alpha_v\beta_3$ interaction inhibitors. Active inhibitor compounds represented by Formula (I), below, are contacted with integrin $\alpha_v\beta_3$ on a cell, which, in turn, inhibits the binding of MMP2 to the $\alpha_v\beta_3$. The inhibition of binding of MMPS to $\alpha_v\beta_3$ by the methods of the present invention result in inhibition of angiogenesis and thus tumor growth. In addition, $\alpha_v\beta_3$ has been implicated in inflammation, thus compounds of Formula (I), used in accordance with the methods of the present invention can also suppress inflammatory events.

Formula (I):

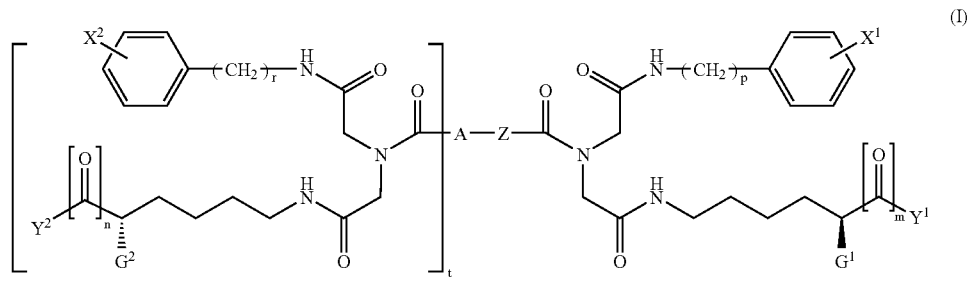

wherein $G^1$ and $G^2$ are each independently —NH—C(O)—O—$R^1$, —NH—C(O)—O—$(CH_2)_v$—$(C_6H_4)$—$X^3$, —NH—C(O)—NH—$(CH_2)_v$—$(C_6H_4)$—$X^3$, —O—C(O)—NH—$(CH_2)_v$—$(C_6H_4)$—$X^3$, —O—C(O)—O—$(CH_2)_v$—$(C_6H_4)$—$X^3$, or —NH—C(O)—$CH_2$—$(C_6H_4)$—$X^3$; $Y^1$ and $Y^2$ are each independently —OH, $C_1$–$C_4$ alkyl, $C_1$–$C_4$ hydroxyalkyl, $C_1$–$C_4$ alkoxy, phenyl, benzyl, or —$NH_2$; $R^1$ is $C_1$–$C_4$ alkyl; $X^1$ and $X^2$ are each independently halo or $C_1$–$C_4$ alkoxy; $X^3$ is halo, nitro, $C_1$–$C_4$ alkyl, $C_1$–$C_4$ alkoxy, or $C_1$–$C_4$ perfluoroalkyl; Z is —C≡C—, —$C_6H_4$—, cis —CH═CH—, trans-CH═CH—, cis-$CH_2$—CH═CH—$CH_2$—, trans-$CH_2$—CH═CH—$CH_2$—, 1,4-naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and p, r, and v are each independently an integer having a value of 1 or 2; with provisos that when A is H, t is 0; when A is a covalent bond, t is 1; when m is 0, $Y^1$ is $C_1$–$C_4$ hydroxyalkyl; and when n is 0, $Y^2$ is $C_1$–$C_4$ hydroxyalkyl.

Preferred compounds within the purview of structural Formula (I) are represented in structural Formula (II):

thus starving it of nutrition. The angiogenesis and tumor growth inhibiting compounds of the present invention are thus useful therapeutic agents for the treatment of patients with tumors or angiogenic disorders. Because the present compounds bind to $α_vβ_3$, these compounds can also be used to suppress inflammatory events.

The compounds of the present invention may be formulated in suitable pharmaceutically acceptable matrix. The pharmaceutical compositions of the active compounds are administered to a patient with a tumor to reduce or eliminate tumor growth. The active compounds can be administered parenterally by injection or by gradual infusion over time, or by any other method suitable for the particular dosage form.

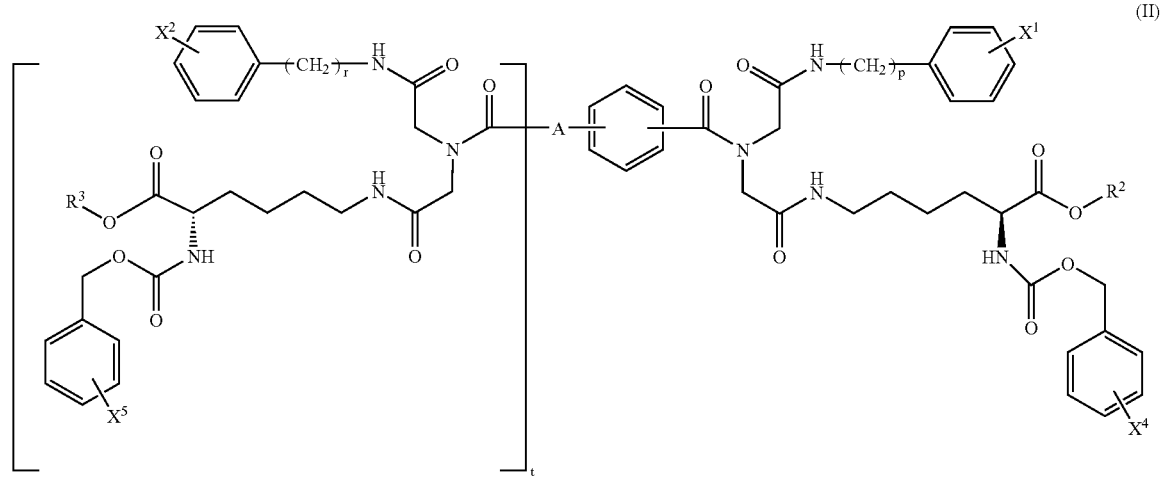

wherein $R^2$ and $R^3$ are each independently H, $C_1$–$C_4$ alkyl, phenyl or benzyl; $X^1$ and $X^2$ are each independently halo or $C_1$–$C_4$ alkoxy; $X^4$ and $X^5$ are each independently halo, nitro, $C_1$–$C_4$ alkoxy, $C_1$–$C_4$ alkyl, or $C_1$–$C_4$ perfluoroalkyl; A is H or a covalent bond; p and r are each independently an integer having a value of 1 or 2; and t is an integer having a value of 0 or 1 with the proviso that when A is H, t is 0 and when A is a covalent bond, t is 1. When A is a covalent bond and t is 1, the iminodiacetamide derivative moieties may be attached to the benzene linking group in the ortho, meta or para position.

Figure 3:
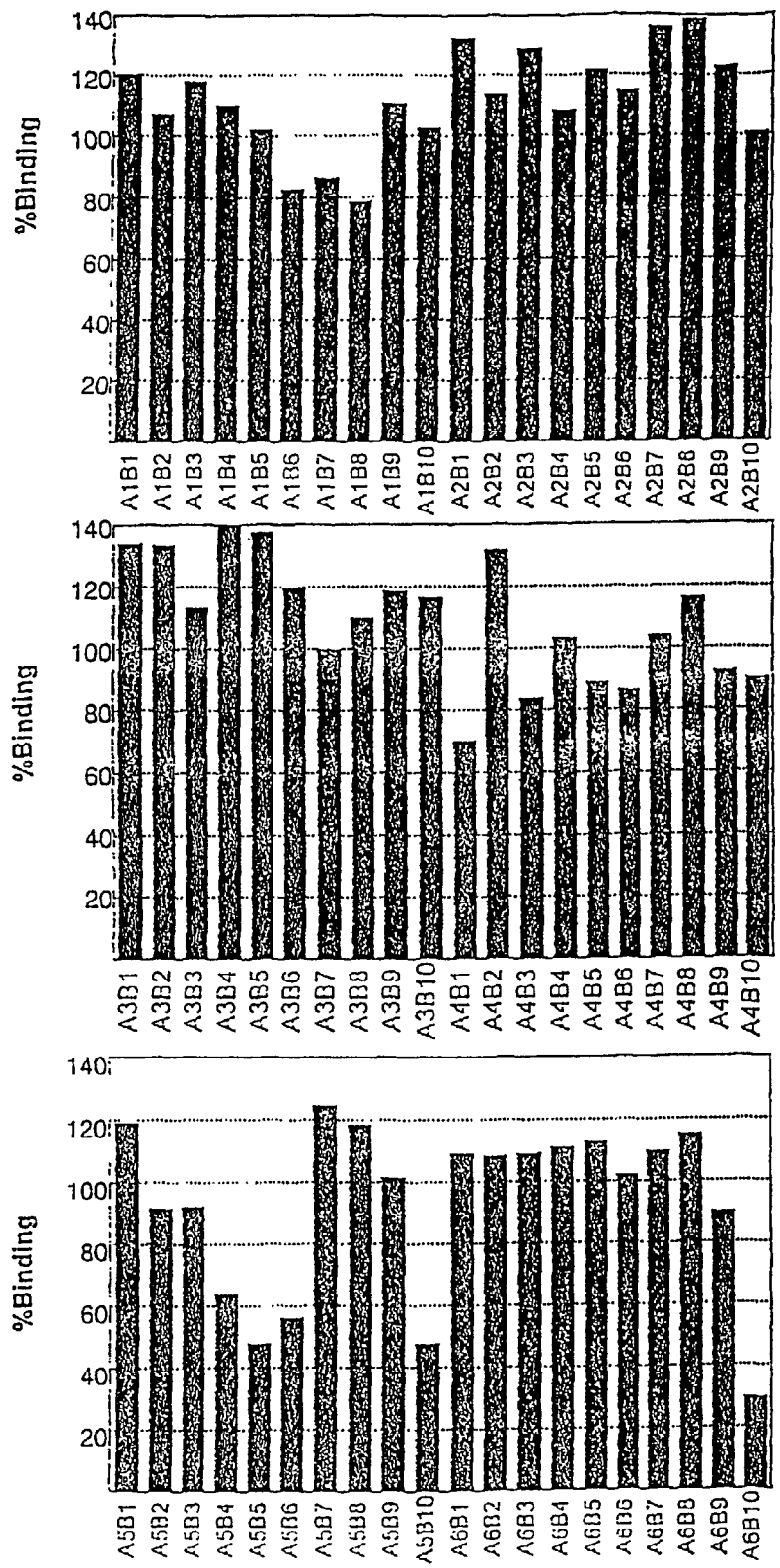

When compounds of Formulas (I) and (II) are contacted with cells containing $α_vβ_3$, the binding of $α_vβ_3$ with MMP2 is inhibited, thus interfering with an essential mechanism in angiogenesis. Interference with angiogenesis can also inhibit tumor growth by preventing vascularization of the tumor, FIG. 3 graphically illustrates the binding of 60 combinatorial mixtures of compounds with integrin $α_vβ_3$ in competition with MMP2.

Figure 4:
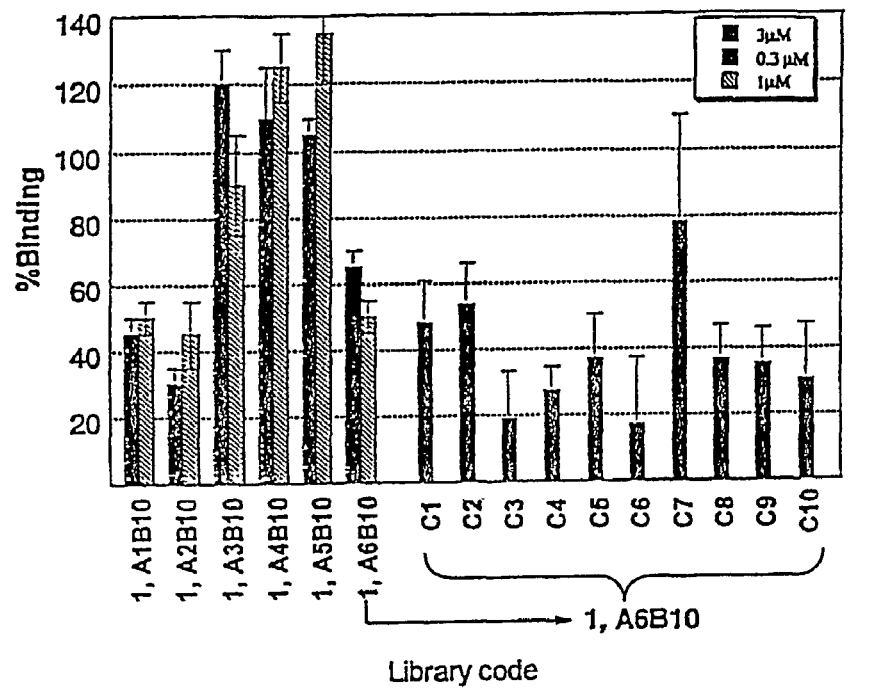
Figure 4:
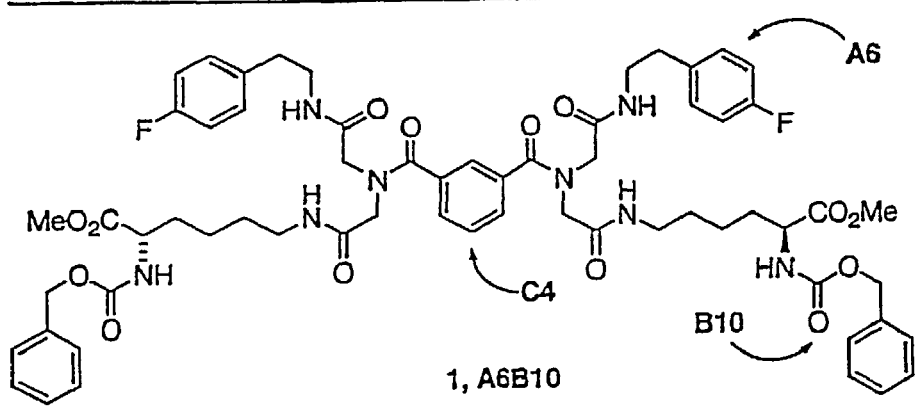

FIG. 4 illustrates the binding of mixtures AxB10 with integrin $α_vβ_3$ and the binding of the 10 individual components of A6B10C4.

Figure 5:
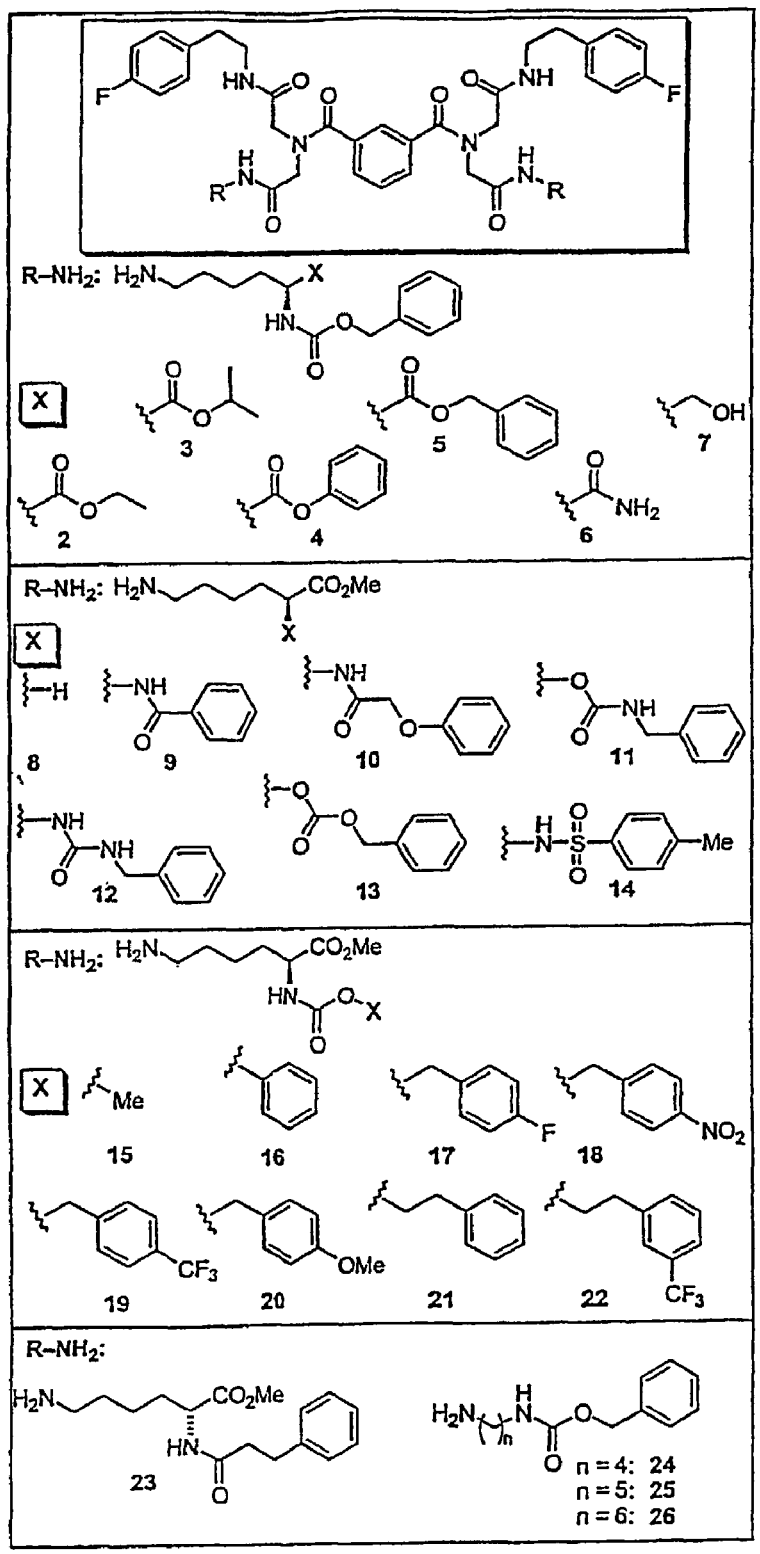

FIG. 5 depicts the structures of analogs of A6B10C4.

Figure 6:
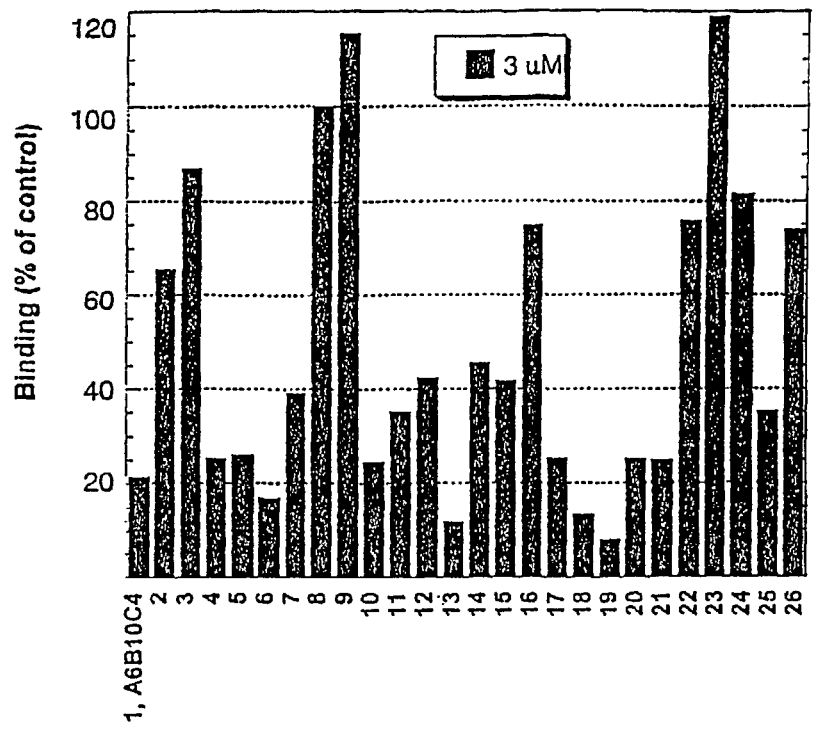
Figure 6:
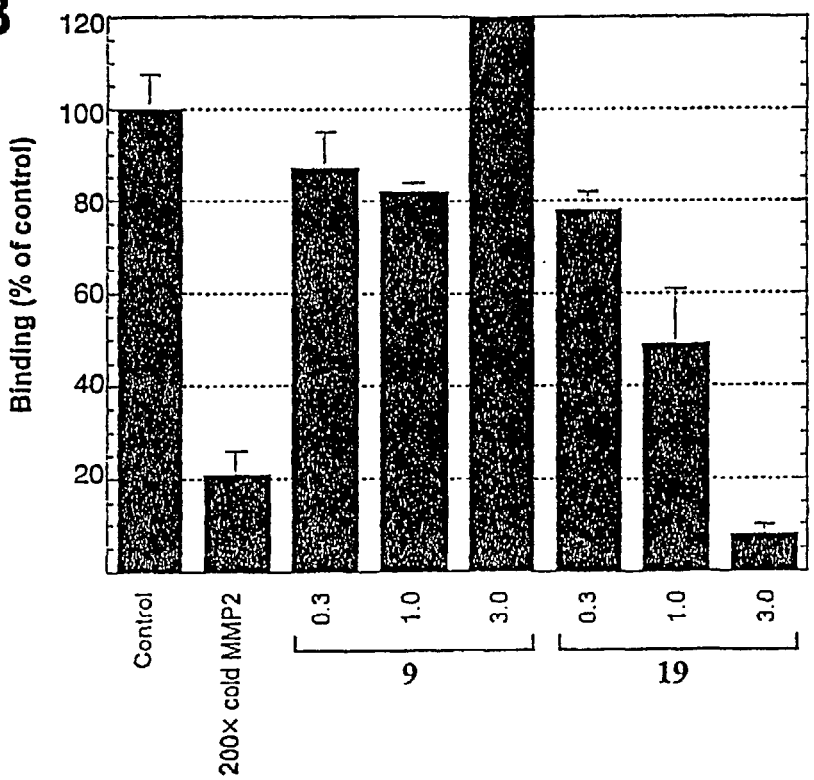

FIG. 6A graphically illustrates the binding of analogs (Compounds 2–26) of A6B10C4 (Compound 1) with integrin $α_vβ_3$ in competition with MMP2.

FIG. 6B graphically illustrates the binding of Compounds 9 and 19 with integrin $α_vβ_3$ in comparison with MMP2.

Figure 7:
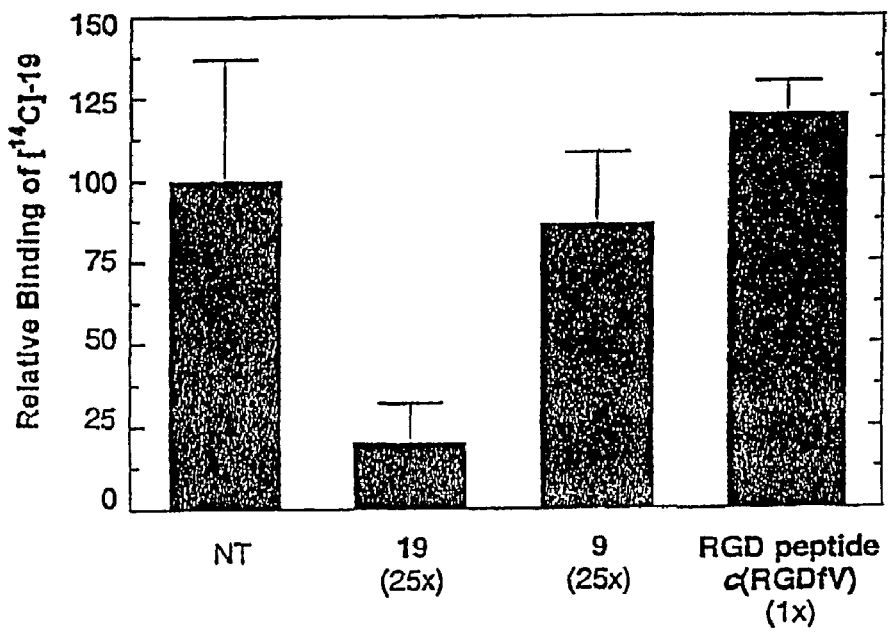

FIG. 7 illustrates that [$^{14}$C]-labeled Compound 19 binds specifically to $α_vβ_3$ and can be competitively displaced from the α$_v$β$_3$ by a 25 fold excess of non-labeled Compound 19, but not by excess Compound 9, a RGD peptide or a c(RGDfV) peptide.

Figure 8:
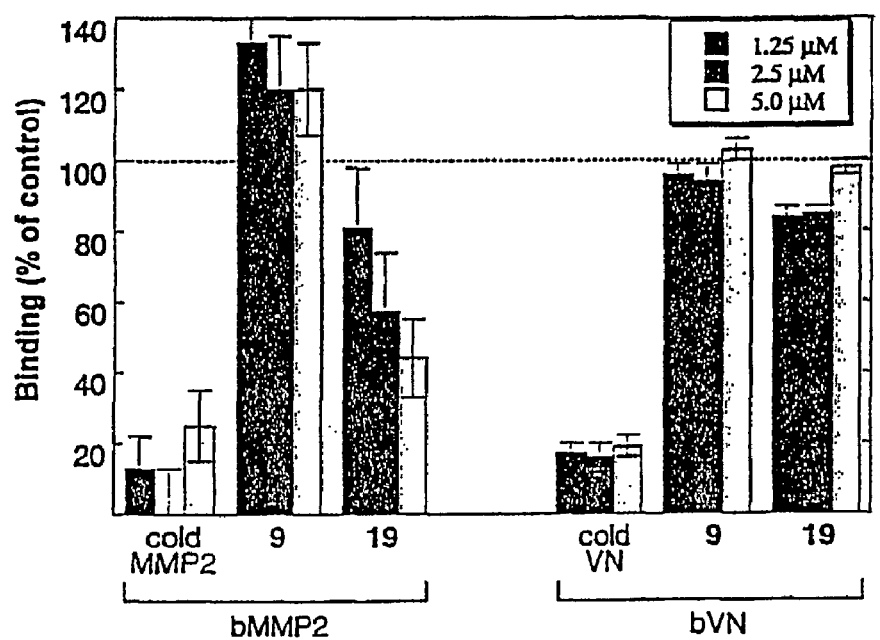

FIG. 8 shows that Compound 19 disrupts the binding of MMP2 to integrin α$_v$β$_3$, but does not interfere with vitronectin binding with integrin α$_v$β$_3$.

Figure 9:
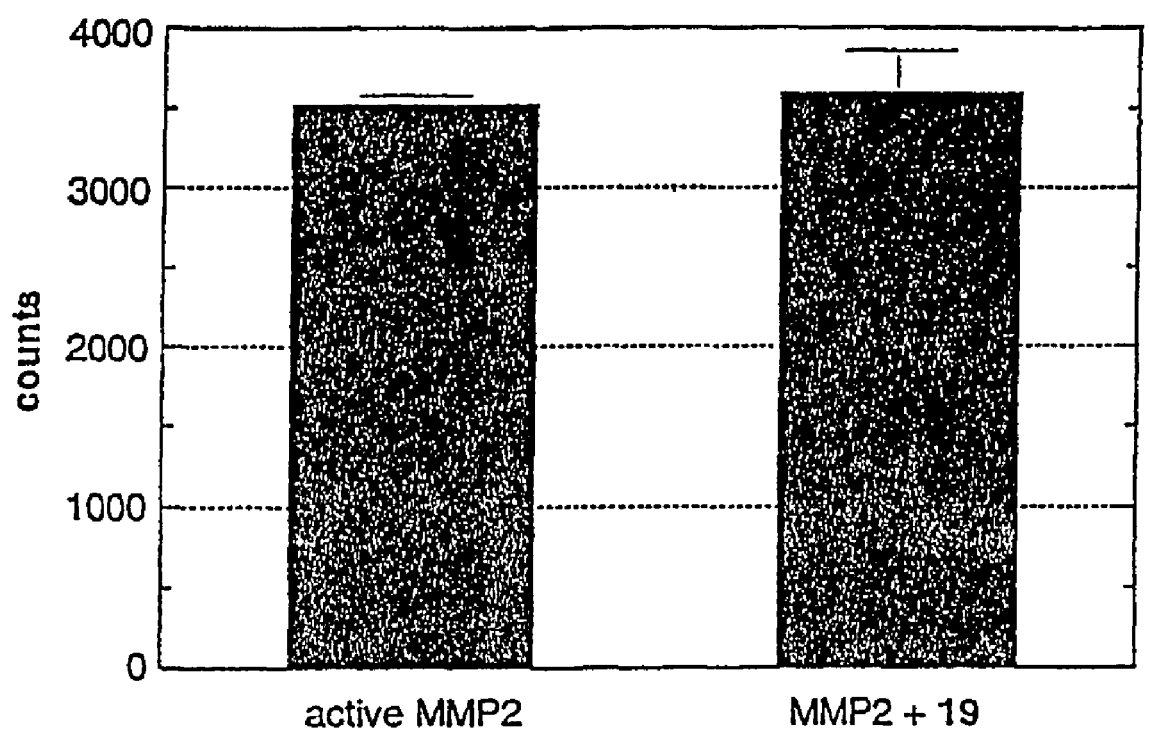

FIG. 9 shows that Compound 19 does not directly inhibit purified active MMP2 proteolysis.

DETAILED DESCRIPTION OF THE INVENTION

Figure 1:
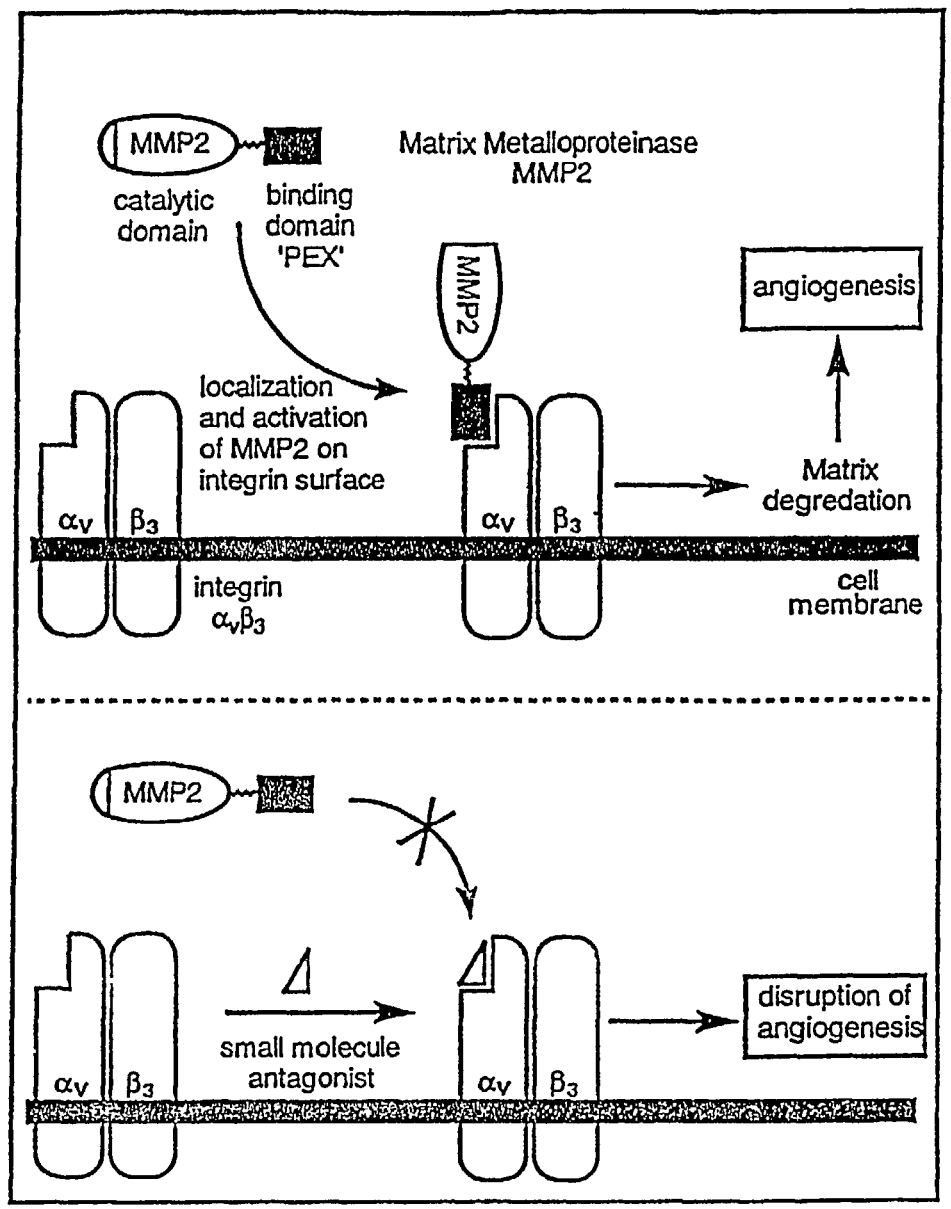
FIG. 1 is a schematic illustration depicting MMP2 interaction with integrin $α_vβ_3$ and its role in angiogenesis.

The binding of MMP2 to integrin α$_v$β$_3$ is an important mechanism in the process of angiogenesis. Specific inhibition of this binding interaction results in a reduction in vascularization in growing tissues such as tumors, and thus retards tumor growth. The interaction of MMP2 with integrin α$_v$β$_3$ is illustrated pictorially in FIG. 1. A new class of angiogenesis and tumor growth inhibitors, described below, specifically bind to integrin α$_v$β$_3$ in competition with MMP2, thus affording an important new treatment tool.

Certain compounds of this invention may possess one or more asymmetric centers and may exist in optically active forms. Additional asymmetric centers may be present in a substituent group, such as an alkyl group. Pure S-isomers and pure R-isomers, racemic mixtures of the isomers, and mixtures thereof are intended to be within the scope of this invention. Chiral forms of certain compounds of this invention are contemplated and are specifically included within the scope of this invention.

The term "alkoxy" means an oxygen atom linked by an ether bond to an alkyl group, as defined below, of the size indicated. Examples of alkoxy groups are methoxy, ethoxy, t-butoxy, and the like. The term "alkyl" means a straight- or branched-chain carbon radical of the size indicated. Representative of alkyl radicals are methyl, ethyl, n-propyl, isopropyl, n-butyl, sec-butyl, isobutyl, t-butyl, 2-ethylhexyl, n-octyl, 2,4-dimethylpentyl, and the like. The term "hydroxyalkyl" means an alkyl group, as defined above, of the size indicated, attached to a hydroxyl group. Examples include hydroxymethyl, 2-hydroxyethyl, 3-hydroxy-1-propyl, 2-hydroxy-1-propyl, 4-hydroxybutyl, and the like.

The term "perfluoroalkyl" refers to a alkyl group of the size indicated, as defined below, bearing fluoro substituents in place of each hydrogen, for example trifluoromethyl and pentafluoroethyl.

The terms "halo" or "halogen" refer to bromo, chloro, fluoro and iodo.

The compounds useful in the methods of the present invention are represented by Formula (I) and include iminodiacetamide derivatives chemically attached to a linking group:

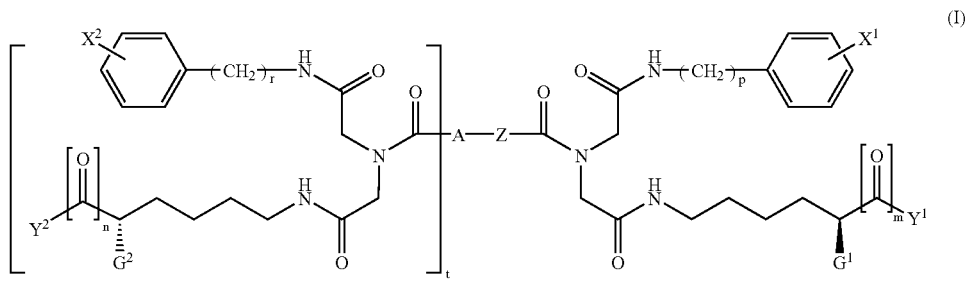

(I)

wherein G$^1$ and G$^2$ are each independently —NH—C(O)—O—R$^1$, —NH—C(O)—O—(CH$_2$)$_v$—(C$_6$H$_4$)—X$^3$, —NH—C(O)—NH—(CH$_2$)$_v$—(C$_6$H$_4$)—X$^3$, —O—C(O)—NH—(CH$_2$)$_v$—(C$_6$H$_4$)—X$^3$, —O—C(O)—O—(CH$_2$)$_v$—(C$_6$H$_4$)—X$^3$, or —NH—C(O)—CH$_2$—(C$_6$H$_4$)—X$^3$; Y$^1$ and Y$^2$ are each independently —OH, C$_1$–C$_4$ alkyl, C$_1$–C$_4$ hydroxyalkyl, C$_1$–C$_4$ alkoxy, phenyl, benzyl, or —NH$_2$; R$^1$ is C$_1$–C$_4$ alkyl; X$^1$ and X$^2$ are each independently halo or C$_1$–C$_4$ alkoxy; X$^3$ is halo, nitro, C$_1$–C$_4$ alkyl, C$_1$–C$_4$ alkoxy, or C$_1$–C$_4$ perfluoroalkyl; Z is —C≡C—, —C$_6$H$_4$—, cis —CH═CH—, trans-CH═CH—, cis-CH$_2$—CH═CH—CH$_2$—, trans —CH$_2$—CH═CH—CH$_2$—, 1,4naphthyl, cis-1,3-cyclohexyl, trans-1,3-cyclohexyl, cis-1,4-cyclohexyl, or trans-1,4-cyclohexyl; A is H or a covalent bond; m and n are each independently an integer having a value of 0 or 1; t is an integer having a value of 0 or 1; and p, r, and v are each independently an integer having a value of 1 or 2; with provisos that when A is H, t is 0; when A is a covalent bond, t is 1; when m is 0, Y$^1$ is C$_1$–C$_4$ hydroxyalkyl; and when n is 0, Y$^2$ is C$_1$–C$_4$ hydroxyalkyl.

Preferred compounds within the purview of structural Formula (I) are represented by structural Formula (II) and include iminodiacetamide derivatives attached to a benzene linking group in either the ortho, meta or para orientation:

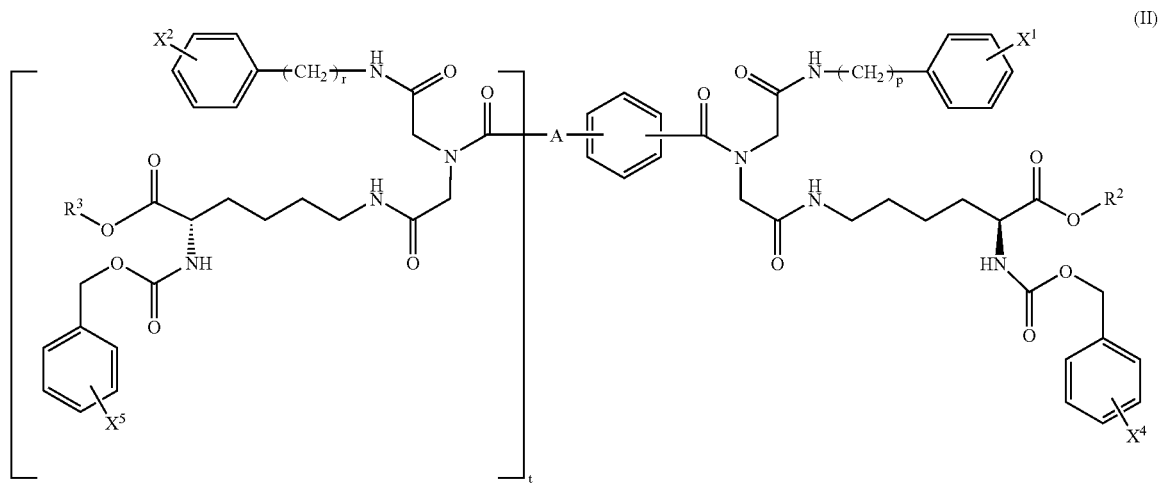

wherein $R^2$ and $R^3$ are each independently H, $C_1$–$C_4$ alkyl, phenyl or benzyl; $X^1$ and $X^2$ are each independently halo or $C_1$–$C_4$ alkoxy; $X^4$ and $X^5$ are each independently halo, nitro, $C_1$–$C_4$ alkoxy, $C_1$–$C_4$ alkyl, or $C_1$–$C_4$ perfluoroalkyl; A is H or a covalent bond; p and r are each independently an integer having a value of 1 or 2; and t is an integer having a value of 0 or 1 with the proviso that when A is H, t is 0 and when A is a covalent bond, t is 1.

Preferably, the substituents $X^1$ and $X^2$ are attached to the phenyl ring in the 4-position relative to the $CH_2$ groups (i.e. para substituent). Preferably, at least one of $X^1$ and $X^2$ is fluoro, most preferably $X^1$ and $X^2$ are both para-fluoro.

Preferably, r and p are 2. $X^4$ and $X^5$ are preferably, $C_1$ to $C_4$ perfluoroalkyl, most preferably para-trifluoromethyl. The preferred $R^2$ and $R^3$ groups are hydrogen and methyl. The substituents $X^2$ and $X^3$ may be the same or different, and the substituents $R^2$ and $R^3$ may also be the same or different.

The compounds of Formulas (I) and (II) are described in detail, along with methods of synthesis thereof, in Boger et al., *Bioorg. Med. Chem*, 6, 1347–1378 (1998), incorporated herein by reference.

A particularly active member of the family of compounds represented by Formula (II), wherein A is a covalent bond and t is 1, is Compound 19 in Scheme 1, below.

Scheme 1.

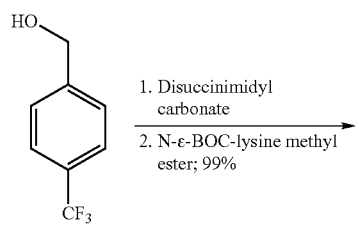

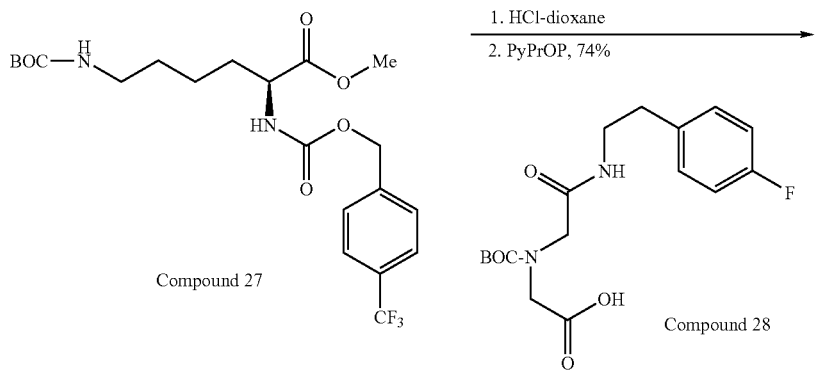

Compound 27

Compound 28

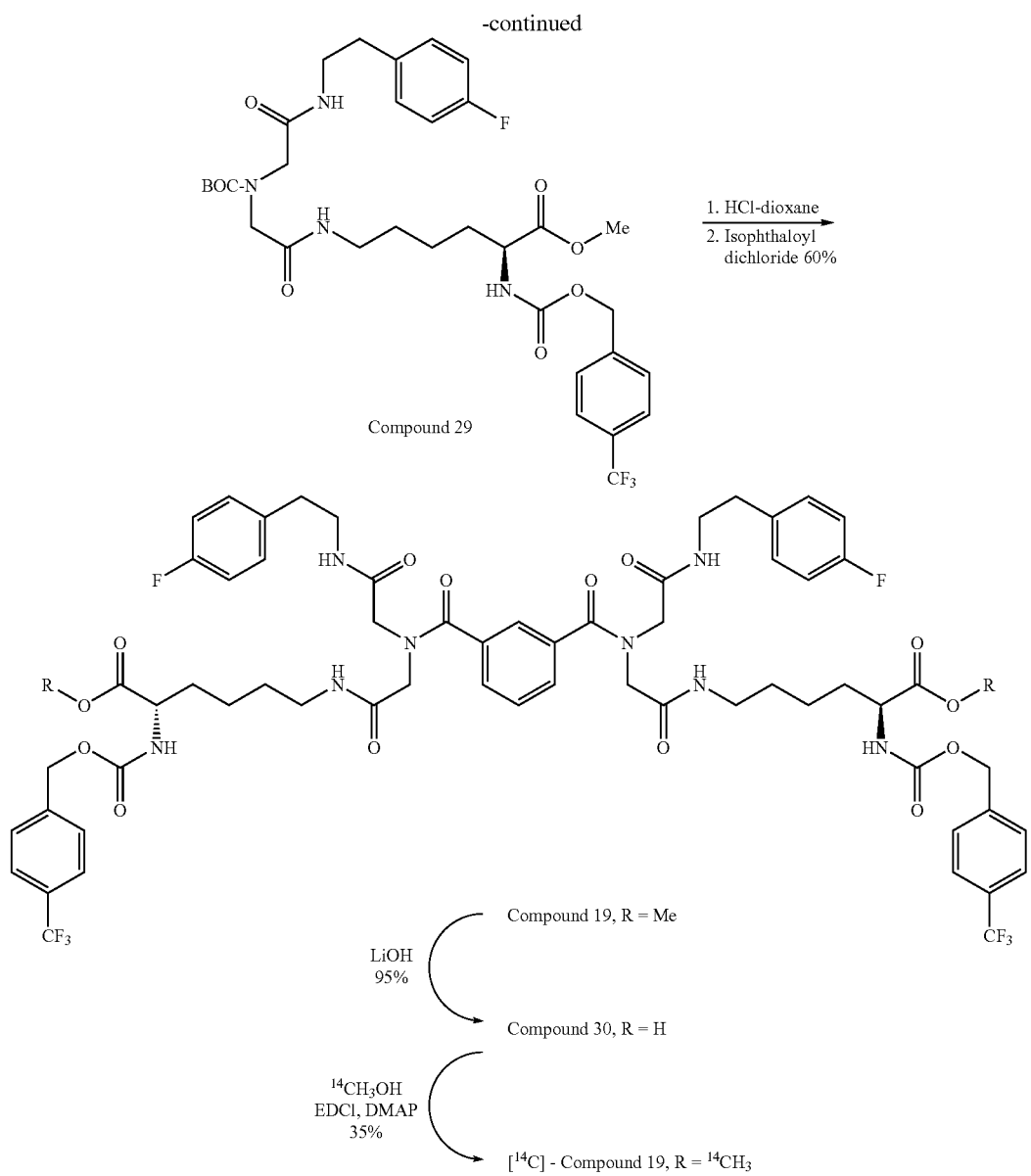

Compound 29

Compound 19, R = Me
Compound 30, R = H
[$^{14}$C] - Compound 19, R = $^{14}$CH$_3$ The synthesis of Compound 19 is illustrative of a general method of producing compounds of Formulas (I) and (II) described by Boger et al. Compound 19 was synthesized in three steps starting with commercially available N-ε-BOC-L-lysine methyl ester. The carbamate was installed in 99% yield by reaction of 4-(trifluoromethyl)benzyl alcohol with N, N-disuccinimidyl carbonate and subsequent addition of the activated product with the free α-amino group providing intermediate Compound 27. This lysine derivative was then subjected to N-BOC deprotection (HCl) and coupled with bromotripyrrolidinophosphonium hexafluorophosphate (Py-BrOP, 74%) to the free carboxylic acid functionality of the iminodiacetic acid monoamide Compound 28 providing diamide Compound 29. After N-BOC deprotection (HCl) this was dimerized by reaction with isophthaloyl dichloride completing the synthesis and providing Compound 19 in 60% yield. A radiolabel was incorporated into the molecule by saponification of the two methyl esters (LiOH, 95%) providing dicarboxylic acid Compound 30, followed by esterification with [$^{14}$C]-methanol mediated by 1-(3-(dimethylamino)propyl)-3-ethylcarbodiimide hydrochloride (EDCI) and catalytic 4-dimethylaminopyridine (DMAP) to afford [$^{14}$C]-Compound 1 in 35% yield.

Pharmaceutical preparations of compounds of Formulas (I) and (II) can be prepared by formulating the compound in a pharmaceutically acceptable carrier matrix. The pharmaceutical compositions comprising the active compounds of Formulas (I) and (II) are administered to a host with a tumor to reduce or eliminate tumor growth. The active compounds can be administered parenterally by injection, or by gradual infusion over time. Although the tissue to be treated is most often treated by intraperitoneal or subcutaneous administration, the active compounds can also be administered intraocularly, intravenously, intramuscularly, intrasynovially, intracavity, or transdermally, and can be delivered by peristaltic means as well.

The term "administration" of the inventive compound or composition, as used herein, refers to systemic use as when taken orally, parenterally, by inhalation spray, by nasal, rectal or buccal routes, or topically in dosage form unit formulations containing conventional nontoxic pharmaceutically acceptable carriers, adjuvants and vehicles as desired. The terra "parenteral" as used herein includes intravenous, intramuscular, intraperitoneal, intrasternal, subcutaneous and intraarticular injection and infusion techniques.

By "pharmaceutically acceptable" it is meant those salts, amides and esters which are, within the scope of sound medical judgement, suitable for use in contact with the tissues of humans and lower animals without undue toxicity, irritation, allergic response and the like, and are commensurate with a reasonable benefit/risk ratio, effective for their intended use in the treatment of tumors and angiogenic-related disorders.

Pharmaceutically acceptable salts are well known in the art. For example, S. M Berge, et al. describe pharmaceutically acceptable salts in detail in J. *Pharmaceutical Sciences,* 66, 1–19 (1977). Representative acid addition salts include hydrochloride, hydrobromide, sulfate, bisulfate, acetate, oxalate, valerate, oleate, palmitate, stearate, laurate, borate, benzoate, lactate, phosphate, toluenesulfonate, methanesulfonate, citrate, maleate, fumarate, succinate, tartrate, ascorbate, glucoheptonate, lactobionate, lauryl sulfate salts and the like. Representative alkali or alkaline earth metal salts include sodium, calcium, potassium, magnesium salts and the like.

As used herein, the term "pharmaceutically acceptable carriers" means a non-toxic, inert solid, semi-solid or liquid filler, diluent, encapsulating material or formulation auxiliary of any type. Some examples of the materials that can serve as pharmaceutically acceptable carriers are sugars, such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols, such as propylene glycol; polyols such as glycerin, sorbitol, mannitol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol and phosphate buffer solutions, as well as other non-toxic compatible substances used in pharmaceutical formulations.

Wetting agents, emulsifiers and lubricants such as sodium lauryl sulfate and magnesium stearate, as well as coloring agents, releasing agents, coating agents, sweetening, flavoring and perfuming agents, preservatives and antioxidants can also be present in the composition, according to the judgement of the formulator. Examples of pharmaceutically acceptable antioxidants include water soluble antioxidants such as ascorbic acid, cysteine hydrochloride, sodium bisulfite, sodium metabisulfite, sodium sulfite, and the like; oil soluble antioxidants such as ascorbyl palmitate, butylated hydroxyanisole (BHA), butylated hydroxytoluene (BHT), lecithin, propyl gallate, alpha-tocopherol and the like; and the metal chelating agents such as citric acid, ethylenediamine tetraacetic acid (EDTA), sorbitol, tartaric acid, phosphoric acid and the like.

By a "therapeutically effective amount" of the inventive agent or compound is meant a sufficient amount of the compound to treat tumors and angiogenic-related disorders at a reasonable benefit/risk ratio applicable to any medical treatment. It will be understood, however, that the total daily usage of the compounds and compositions of the present invention will be decided by the attending physician within the scope of sound medical judgement. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidently with the specific compound employed; and like factors well known in the medical arts.

This invention also provides pharmaceutical compositions in unit dosage forms, comprising a therapeutically effective amount of a compound (or compounds) of this invention in combination with a conventional pharmaceutical carrier. Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides.

In addition, fatty acids such as oleic acid are used in the preparation of injectables. The injectable formulation can be sterilized, for example, by filtration through a bacteria-retaining filter, or by incorporating sterilizing agents in the form of sterile solid compositions which can be dissolved or dispersed in sterile water or other sterile injectable medium just prior to use.

In order to prolong the effect of a drug, it is often desirable to slow the absorption of a drug from subcutaneous or intramuscular injection. The most common way to accomplish this is to inject a suspension of crystalline or amorphous material with poor water solubility The rate of absorption of the drug becomes dependent on the rate of dissolution of the drug which is, in turn, dependent on the physical state of the drug, for example, the crystal size and the crystalline form. Another approach to delaying absorption of a drug is to administer the drug as a solution or suspension in oil. Injectable depot forms can also be made by forming microcapsule matrices of drugs and biodegradable polymers such as polylactide-polyglycolide. Depending on the ratio of drug to polymer and the composition of the polymer, the rate of drug release can be controlled. Examples of other biodegradable polymers include poly-orthoesters and polyanhydrides. The depot injectables can also be made by entrapping the drug in liposomes or microemulsions which are compatible with body tissues.

Suppositories for rectal administration of the drug can be prepared by mixing the drug with a suitable nonirritating excipient such as cocoa butter and polyethylene glycol which are solid at ordinary temperature but liquid at the rectal temperature and will therefore melt in the rectum and release the drug.

Solid dosage forms for oral administration may include capsules, tablets, pills, powders, prills and granules. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. Tablets and pills can additionally be prepared with enteric coatings and other release-controlling coatings. Solid compositions of a similar type may also be employed as fillers in soft and hard-filled gelatin capsules using such excipients as lactose or milk sugar as well as high molecular weight polyethylene glycols and the like.

Liquid dosage forms for oral administration may include pharmaceutically acceptable lo emulsions, microemulsions, solutions, suspensions, syrups and elixirs containing inert diluents commonly used in the art such as water. Such compositions may also comprise adjuvants, such as wetting agents; emulsifying and suspending agents; sweetening, flavoring and perfuming agents. If desired, the compounds of the present invention can be incorporated into slow release or targeted delivery systems such as polymer matrices, liposomes and microspheres. They may be sterilized, for example, by filtration through a bacteria-retaining filter, or by incorporating sterilizing agents in the form of sterile solid compositions which can dissolve in sterile water, or some other sterile injectable medium immediately before use. The active compounds can also be in micro-encapsulated form with one or more excipients as noted above.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferably, in a certain part of the intestinal tract, optionally in a delayed manner. Examples of embedding compositions which can be used include polymeric substances and waxes. Dosage forms for topical or transdermal administration of a compound of this invention further include ointments, pastes, creams, lotions, gels, powders, solutions, sprays, inhalants or patches. The active component is admixed under sterile conditions with a pharmaceutically acceptable carrier and any needed preservatives or buffers as may be required.

Ophthalmic formulations, ear drops, eye ointments, powders and solutions are also contemplated as being within the scope of this invention. The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispersing the compound in the proper medium. Absorption enhancers can also be used to increase the flux of the compound across the skin. The rate can be controlled by either providing a rate controlling membrane or by dispersing the compound in a polymer matrix or gel.

The compositions containing the active compounds can be administered in a manner compatible with the dosage formulation and in a therapeutically effective amount. The quantity to be administered and the timing of administration depend on the host to be treated, capacity of the host's system to utilize the active ingredient, and degree of therapeutic effect desired. Precise amounts of the active ingredient required to be administered depend on the judgment of the practitioner, and are peculiar to each individual.

Suitable dosage ranges for systemic application are disclosed herein and depend on the route of administration. Suitable regimes for administration are also variable, but are typified by an initial administration, followed by repeated doses at one or more predetermined intervals by a subsequent injection or other route of administration.

The present invention also provides a pharmaceutical composition useful for practicing the therapeutic methods described herein. The compositions contain an active compound described hereinabove, together with a pharmaceutically acceptable carrier.

Preparations for parental administration of the present compounds or compositions include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parental vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present, such as, for example, antimicrobials, antioxidants, chelating agents, inert gases, and the like.

Another aspect of the present invention provides a method for inhibiting MMP2 interaction with $\alpha_v\beta_3$ and thus angiogenesis in a tumor tissue. The inhibiting method comprises administering to the host a composition comprising an angiogenesis-inhibiting amount of a compound described hereinabove. MMP2 interaction with $\alpha_v\beta_3$ is inhibited by contacting $\alpha_v\beta_3$ with a compound of the present invention.

Angiogenesis is the formation of a neovascular network from pre-existing host vessels and is required for tumor growth beyond 1–2 mm$^3$. For the purpose of the present invention, angiogenesis is inhibited as long as angiogenesis and the disease symptoms mediated by angiogenesis are ameliorated.

The dosage ranges for the administration to a host of the active compound depend upon the particular active compound and its potency to a particular tumor or integrin. One skilled in the art can readily determine the proper dosage for a particular active compound without undue experimentation. The host can be any mammal. The dosage should be large enough to produce the desired therapeutic effect in which angiogenesis and the disease symptoms mediated by angiogenesis are ameliorated, and is usually an amount sufficient to maintain a plasma level of the active compound in the range of about 0.01 to about 100 micromolar (μM), preferably about 0.2 to about 20 μM, more preferably about 1 to about 10 μM. The dosage should not be so large as to cause adverse side effects, however. The dosage per kilogram (kg) of body weight can vary from 1 to 20 mg per dose, in one or more dose administrations daily, for one or several days or indefinitely.

For inhibition of angiogenesis, the therapeutically effective amount is an amount of active compound sufficient to produce a measurable inhibition of angiogenesis in the tissue being treated, i.e., an angiogenesis-inhibiting amount or an MMP2-$\alpha_v\beta_3$ interaction inhibiting amount. Inhibition of angiogenesis can be measured in situ by immunohistochemistry, as described herein, or by other methods known to one skilled in the art.

The present invention additionally provides pharmaceutical compositions useful for practicing the therapeutic methods described herein. The compositions contain an active compound defined hereinabove together pharmaceutically acceptable carrier.

The present invention also provides a method of inducing apoptosis in tumor cells. This method comprises administering to the host a therapeutically effective amount of an active compound sufficient to initiate tumor cell apoptosis.

For the purpose of the present invention, tumor cell apoptosis is induced if an increased tumor cell apoptosis is observed in the target tumor being treated. Tumor cell apoptosis can be measured by methods described herein or commonly known in the art.

The following non-limiting examples are provided to illustrate various aspects of the present invention.

Materials and Methods

Antibodies Cells and Reagents. CS-1 hamster melanoma cells and CS-1 cells transfected with the human $\beta_3$-integrin subunit ($\beta_3$CS-1 cells) were described previously (*Cell*, 85, 683–93 (1996); *Cell*, 92, 391–400 (1998)). The horseradish peroxidase (HRP)—conjugated monoclonal antibodies anti-biotin mAb BN-34 and anti-actin mAb AC-40 were obtained from Sigma (St. Louis, Mo). Anti-von Willebrand Factor (vWF) polyclonal antibodies (pAb) were obtained from DAKO (Glostrup, Denmark). The cyclic peptides cRGDfV and cRADfV and integrin—$\alpha_v\beta_3$ were provided by Merck KGaA (Darmstadt, Germany). Purified proMMP2 and integrin-$\alpha_v\beta_3$ were provided by Chemicon International (Temecula, Calif.). Purified active MMP2 was obtained from Calbiochem (La Jolla, Calif.). Basic fibroblast growth factor (bFGF) was kindly provided by Scios (Mountain View, Calif.).

EXAMPLE 1

Solid Phase Integrin Binding Assays

Purified integrins were adsorbed overnight onto microtiter wells (1–5 µg/ml, 50 µg/well) prior to blocking with Casein-blocker (Pierce, Rockford, Ill.). Purified biotinylated MMP2 (bMMP2, 3–5 nM) in binding buffer (50 mM Tris, pH 8, 150 mM NaCl, 1 mM $MgCl_2$, 0.5 mM $MnCl_2$) was added to the wells in the presence or absence of test compounds, cyclic RGD or RAD peptides, or buffer vehicle alone. Control wells received no integrin. Biotinylated vitronectin (bVN, 1 µg/ml) was used as a reference. Bound protein was detected with HRP-anti-biotin mAb and quantitated at 450 nm with 3,3',5,5'-tetramethylbenzidine solution (TMB; a substrate for the peroxidase) (BioRad, Hercules, Calif.).

For the assessment of direct integrin binding by Compound 19, $\alpha_v\beta_3$ and $\alpha_v\beta_5$ (10 µg/ml, 50 µl/well) were coated onto Immulon-4 microtiter wells (Dynatech Laboratories, Chantilly, Va.), which were substantially blocked and incubated with titration of [$^{14}$C]-Compound 19 prior to the addition of 150 µl of binding buffer containing 0.1% Tween-20 and aspiration of all liquid. Dried wells were separated and immersed in BetaMax liquid scintillation cocktail (ICN Biochemicals, Costa Mesa, Calif.) for quantitation. From this binding curve a subsaturating concentration (3 µM) of [$^{14}$C]-Compound 19 was examined in the presence and absence of a 25-fold molar excess (75 µl) of unlabeled Compound 19 or Compound 9, or 100 µM cyclic RGD or RAD peptide. Control was bVN, used and detected as described above.

EXAMPLE 2

MMP2 Cell-Binding and [$^3$H]-Collagen IV Degradation Assays

CS-1 cells or $\beta_3$CS-1 cells were incubated in adhesion buffer fibroblast basal medium (FBM) supplemented with 0.5% bovine serum albumin (BSA), 0.4 mM $MnCl_2$ and 10 µg/ml aprotinin) containing either 4 nM purified active MMP2 alone, or in combination with 10 µM Compound 19 or Compound 9 for 45 minutes at 37° C. prior to washing and addition to the [$^3$H]-collagen IV-coated wells. Wells had been coated overnight with 50 µl of 0.414 mCi/ml [$^3$H]-collagen IV (ICN Biochemicals, Costa Mesa, Calif.) and washed extensively until the radioactivity in the recovered wash solution reached background. Alternatively, cells were treated as above in the absence of MMP2 or the MMP2 solutions were added directly to the wells without cells, as controls. Collagen IV degradation was quantitated by measuring the radioactivity released into the 50 µl of culture medium as determined in a liquid scintillation counter. For the assessment of biotinylated MMP2 binding to CS-1 cells, cells were suspended in adhesion buffer and incubated with 12 nM bMMP2 for 45 minutes at 37° C. in the presence or absence of 10 µM Compound 19 or Compound 9. Cells were subsequently washed before lysis and processing for SDS-PAGE and immunoblotting with an anti-biotin mAb.

EXAMPLE 3

Synthesis of Compound 27

A solution of N,N'-disuccinimidyl carbonate 95.38 g, 21 mmol) in acetonitrile (150 mL) was treated with 4-(trifluoromethyl)benzyl alcohol (2.87 mL, 21 mmol) and triethylamine ($Et_eN$; 5.8 mL, 42 mmol) and stirred at 25° C. After 3 h this solution was added to a flask containing N-$\epsilon$-BOC-lysine methyl ester (4.2 g, 14 mmol) in acetonitrile and stirred for an additional 3 h. The solvent was evaporated and the residue dissolved in $CH_2Cl_2$ (250 mL) and washed with 10% hydrochloric acid (2×200 mL) and saturated aqueous $NaHCO_3$ (200 mL). Flash chromatography ($SiO_2$, 3:1 $CH_2Cl_2$/EtOAc) provided 6.4 g (99%) of Compound 27 as a pale yellow oil: $[\alpha]_D^{25}$ –8.9 ©5.55, $CH_3OH$; $^1$H NMR ($CDCl_3$, 400 MHz) δ 7.57 (d, J=8.1 Hz, 2H), 7.39 (d, J=8.1 Hz, 2H), 5.70 (d, J=7.9 Hz), 5.13 (m, 2H), 4.71 (m, 1H), 4.28 (m, 1H), 3.67 (s, 3H), 3.03 (m, 2H), 1.78 (m, 1H), 1.64, (m, 1H) 1.46–1.32 (m, 4H) 1.35 (s, 9H); $^{13}$C NMR ($CDCl_3$, 100 MHz) δ 172.9, 156.2, 155.8, 140.4, 130.1 (q, J=32.0 Hz), 127.8, 125.3, 122.9 (q J=270.0 Hz), 79.05, 65.8, 53,7, 52.3, 39.8, 31.7, 29.5, 28.4, 22.2; IR (film) $v_{max}$ 3357, 2952, 1790, 1745, 1524 $cm^{-1}$; FABHRMS (NBA-NaI) m/z 463.2044 ($M+H^+$, $C_{21}H_{29}F_3N_2O_6$ requires 463.2056).

EXAMPLE 4

Synthesis of Compound 29

A solution of Compound 27 (2.2 g, 48.8 mmol) in $CH_2Cl_2$ (3 mL) was treated with 4 N HCl-dioxane (10 mL) and stirred for 20 min at 25° C. Solvent and excess acid were removed under reduced pressure, and the crude hydrochloride salt was dissolved in DMF (40 mL), treated with N-((tert-butyloxy)carbonyl)-N'-(2-(4-fluorophenyl)ethyl) iminodiacetic acid monoamide (Compound 28) (1.68 g, 4.8 mmol), PyBrOP (3.3 g, 7.1 mmol) and diisopropylethylamine (i-Pr$_2$NEt; 5.0 mL, 29 mmol) and stirred for 1 h at 25° C. The reaction mixture was diluted with EtOAc (400 mL) and washed with 10% aqueous HCl (2×300 mL) and saturate aqueous NaHCO$_3$ (300 mL). Flash chromatography (SiO$_2$, 1:1 CH$_2$Cl$_2$/EtOAc) provided 2.47 g (74%) of Compound 29 as a white foamy solid: $[\alpha]_D^{25}$–7.1 ©4.50, CH$_3$OH); $^1$H NMR (CDCl$_3$, 400 MHz) δ 8.23 and 7.59 (m, together 1H), 7.58 (d, J=8.1 Hz, 2H), 7.43 (m, 2H), 7.13 (m, 2H), 7.06 and 6.78 (m, together 1H), 6.94 (m, 2H), 5.70 (dd, J=12.9 and 8.2 Hz, 1H), 5.11 (m, 2H), 4.31 (m, 1H), 3.85–3.72 (m, 4H), 3.71 (s, 3H, 3.49 (m, 2H), 3.22 (m, 2H), 2.79 (m, 2H), 1.81–1.39 (m, 6H] 1.38 (s, 9H); ⁻C NMR (CDCl$_3$, 100 MHz) δ 172.8, 170.0, 169.9, 155.8, 154.8, 161.4 (d, J=242.7 Hz), 140.2, 134.4, 130.1 (q, J=33.4 Hz), 130.0, 127.7, 125.3 (q, J=3.0 Hz), 123.8 (q, J=299.9 Hz), 115.0, 81.2, 65.7, 53.9, 53.3, 52.2, 40.8, 38.6, 34.4, 31.5, 28.0, 22.4; IR (film) $v_{max}$ 3267, 2935, 1708, 1657, 1511 cm$^{-1}$; FABHRMS (NBA-CsI) m/z 831.2026 (M+Cs$^+$, C$_{33}$H$_{42}$F$_4$N$_4$O$_8$ requires 831.1993).

EXAMPLE 5

Synthesis of Compound 19

A solution of Compound 29 (50 mg, 0.075 mmol) in CH$_2$Cl$_2$ (1 mL) was treated with 4 N HCl-Dioxane (1 mL) and stirred for 1 h at 25° C. Solvent and excess acid were removed under a stream of N$_2$, and the crude hydrochloride salt was suspended in CH$_2$Cl$_2$ (1 mL) and treated with isophthaloyl dichloride (7.6 mg, 0.038 mmol), and i-Pr$_2$NEt (0.05 mL, 0.3 mmol) and stirred for 12 h at 25° C. The reaction mixture was diluted with EtOAc (50 mL) and washed with 10% hydrochloric acid (3×30 mL), saturated aqueous NaHCO$_3$ (30 mL) and saturated aqueous NaCl (30 mL). Flash chromatography (SiO$_2$, 1:4.5:4.5 MeOH/CH$_2$Cl$_2$/EtOAc) provided 30 mg (60%) of Compound 19 as a white powder: $^1$H NMR (CD$_3$OD, 400 MHz) δ 7.62 (m, 4H), 7.52 (m, 4H), 7.42 (m, 4H), 7.19 (m, 4H), 6.96 (m, 4H), 5.14 (m, 4H), 4.16 (m, 2H), 4.13 (m, 2H), 4.08 (m, 2H), 3.99 (m, 4H), 3.68 (s, 6H), 3.45–3.35 (m, 4H), 3.25–3.11 (m, 4H), 2.82–2.70 (m, 4H), 1.82 (m, 2H), 1.69 (m, 2H) 1.60–1.34 (m 8H); IR (film) $v_{max}$ 3291, 2936, 1725, 1651, 1326 cm$^{-1}$; FABHRMS (NBA-CsI) m/z 1459.4015 (M+Cs$^+$, C$_{64}$H$_{70}$F$_8$N$_8$O$_{14}$ requires 1459.3938).

EXAMPLE 6

Synthesis of Compound 30

A solution of Compound 19 (13 mg, 0.01 mmol) in tert-butanol (0.3 mL) was treated with LiOH.H$_2$O (0.91 mg, 0.22 mmol) dissolved in H$_2$O (0.15 mL), and stirred for 2 h at 0° C. The reaction mixture was then quenched with HCO$_2$H (1 mL), diluted with EtOAc (10 mL) and washed with saturated aqueous NaCl (2×10 mL). Drying (Na$_2$SO$_4$) and evaporation provided 12 mg (95%) of Compound 30 as a white powder: $^1$H NMR (DMSO-d$_6$, 400 MHz) δ 12.54 (br s,2H), 8.63 (m, 1H), 8.43 (m, 2H), 8.30 (m, 1H), 7.74 (m, 4H), 7.69 (m, 2H), 7.57 (m, 4H), 7.40 (m, 4H), 7.24 (m, 4H), 7.09 (m, 4H), 5.15 (m, 4H), 4.14 (m, 2H), 4.02–3.87 (m, 8H), 3.31 (m, 4H), 3.208 (m, 4H), 2.74 (m, 4H), 1.71 (m, 2H), 1.62 (m, 2H) 1.50–1.34 (m, 8H; IR (film) $v_{max}$ 3287, 2928, 1705, 1659, 1320 cm$^{-1}$; MALDIHRMS m/z 1321.4493 (M+Na$^+$, C$_{62}$H$_{66}$F$_8$N$_8$O$_{14}$ requires 1321.4468).

EXAMPLE 7

Synthesis of [$^{14}$C]-Compound 19

A solution of Compound 27 (1.7 mg, 1.3 mmol) and EDCI (2.0 mg, 10.3 mmol) in DMF (20 mL) was treated with 0.3 mL of a solution of $^{14}$CH$_3$OH in CH$_2$Cl$_2$ (57 mCi/mmol, 5.2 mmol $^{14}$CH$_3$OH) and 35 mL of DMAP stock solution in CH$_2$Cl$_2$ (0.6 mmol DMAP) and stirred for 4 h at 0° C. The reaction mixture was then diluted with EtOAc (3 L) and washed with 10% hydrochloric acid (3×3 mL) and saturated aqueous NaHCO$_3$ (3 mL) and dried (Na$_2$SO$_4$). Purification on PTLC (SiO$_2$, 2:3:3 EtOH/CHCl$_3$EtOAc) provided 0.6 mg (35%) of [$^{14}$C]-Compound 19 as a white film. This material was identical to the corresponding unlabeled dimethyl ester Compound 1 by $^1$H NMR and HPLC. The relative activity was approx. 104 mCi/mmol: $^1$H NMR (CD$_3$OD, 400 MHz) δ 7.62 (m, 4H), 7.52 (m, 4H), 7.42 (m, 4H), 7.19 (m, 4H), 6.96 (m, 4H), 5.14 (m, 4H), 4.16 (m, 2H), 4.13 (m, 2H), 4.08 (m, 2H), 3.99 (m, 4H), 3.68 (s, 6H), 3.45–3.35 (m, 4H), 3.25–3.11 (m, 4H), 2.82–2.70 (m, 4H), 1.82 (m, 2H), 1.69 (m, 2H) 1.60–1.34 (m, 8H).

Results and Discussion

Figure 2:
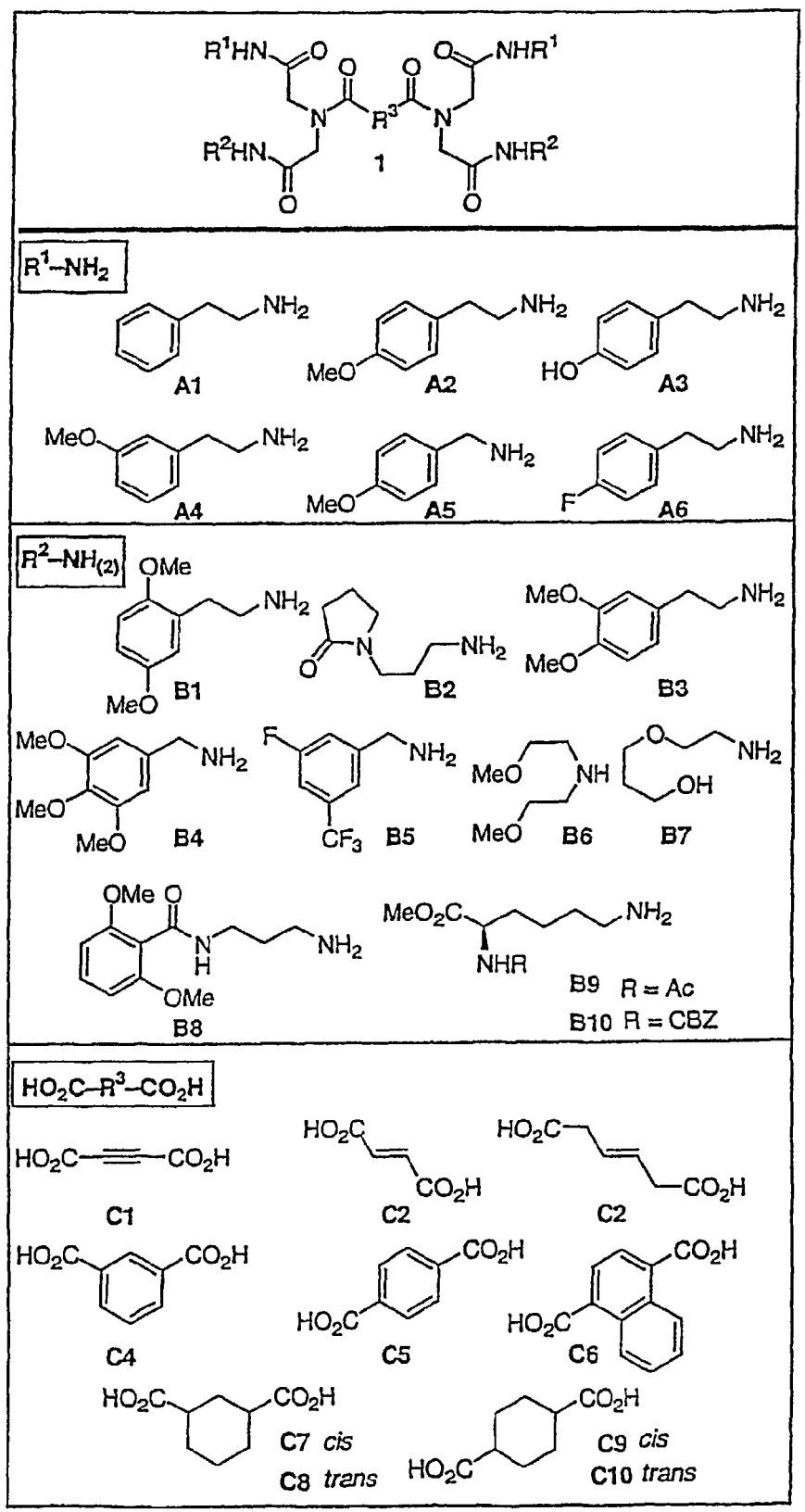
FIG. 2 depicts the structural subunits A, B and C of a combinatorial library of 600 compounds disclosed in Boger et al., *Bioorg. Med. Chem*, 6, 1347–1378 (1998).

Combinatorial libraries of compounds, including compounds of Formulas (I) and (II) are described in detail, along with methods of synthesis thereof, in Boger et al., *Bioorg. Med. Chem*, 6, 1347–1378 (1998). Boger et al. describe the preparation of a combinatorial library of 60 mixtures of 10 compounds each wherein the individual compounds in the mixtures are comprised of three subunits coupled together as shown in FIG. 2. The subunits of the compounds are designated A, B and C. The library was constructed from six different A units (A1–A6), 10 different B units (B1–B10), and 10 different C linking groups (C1–C10). Each A unit was coupled to each B unit, to form 60 distinct AB compounds. The individual AB compounds were then coupled to mixtures of ten different C linking groups, to form 60 mixtures of 10 compounds each, designated AxBy wherein the x and y denote the individual A and B subunits, respectively, that were incorporated into the compounds of the mixtures. The A, B and C subunits of the combinatorial library of compounds are shown in FIG. 2.

Evaluation of the 60 mixtures described hereinabove in a competitive integrin α$_v$β$_3$ binding assay, in competition with MMP2 indicated that several of the mixtures inhibited the binding of MMP2 with integrin α$_v$β$_3$. The results of the evaluation assay are presented in FIG. 3. The particularly active mixtures included A1B6, A1B7, A1B8, A4B1, A5B4, A5B5, A5B6, A5B10, and A6B10. The most active mixture was A6B10, therefore, the ten individual compounds of the mixture were synthesized separately and examined in the same assay, the results of which are presented in FIG. 4. All of the individual components A6B10C1 through A6B10C10 were active at a 3 μM concentration in the assay.

Analogs Compounds (2–26) of A6B10C4 (Compound 1), shown in FIG. 5, were also evaluated. The results of the binding assays for Compounds 2–26 are presented in FIG. 6A. All of the compounds except Compounds 8, 9 and 23 inhibited MMP2 binding to integrin.

The active MMP2/integrin-$\alpha_v$-$\beta_3$ binding inhibitors of present invention are encompassed by Formulas (I) and (II).

Compound 19 was examined in detail to determine its specific target and to define its biological properties. Benzoyl amide Compound 9 was selected as an appropriate negative control compound for many of these studies since it was found to lack antagonist activity in the binding assay, despite its overall structural similarity and similar physical properties (e.g. solubility and hydrophobicity). Compound 19 exhibited concentration dependent inhibition of binding of MMP2 to integrin as shown in FIG. 6B.

A radiolabel ($^{14}$C) was incorporated into Compound 19 in the ester substituent (relative activity approx. 104 mCi/mmol). After incubation (at 3 μM) with fixed $\alpha_v\beta_3$ and subsequent washing, this compound was found to adhere to the integrin as demonstrated in FIG. 7. Incubation in the presence of a 25-fold molar excess of cold Compound 19 significantly reduced the observed amount of bound agent, whereas incubation in the presence of a 25-fold molar excess of (cold) control Compound 9 did not affect the binding of [$^{14}$C]-Compound 19. In a similar experiment measuring the interaction of [$^{14}$C]-Compound 19 to fixed MMP2, no binding was observed. These results suggest that the origin of the antagonist activity observed in the MMP2-$\alpha_v$-$\beta_3$ binding assay is derived from the specific binding of Compound 19 to $\alpha_v$-$\beta_3$. The nature of the Compound 19-$\alpha_v$-$\beta_3$ interaction is independent from the integrin site which recognizes the Arg-Gly-Asp sequence. Cyclic RGD peptide cyclo(Arg-Gly-Asp-D-Phe-Val) had no effect on [$^{14}$C]-Compound 19 binding (FIG. 7). In fact, as shown in FIG. 8, Compound 19 did not inhibit the binding of vitronectin, $\alpha_v\beta_3$'s classical high-affinity ligand to the integrin, consistent with the concept that the binding site for Compound 19 is distinct from that which binds RGD-ligands.

Compound 19 was also studied in a cellular assay, which measures the ability of endothelial cells to utilize MMP2 to degrade a protein matrix, a key step in angiogenesis. It has been shown previously that disrupting the binding of MMP2 to $\alpha_v\beta_3$ inhibits collagen IV degradation. CS-1 melanoma cells transfected with $\alpha_v\beta_3$ were found to degrade immobilized [$^3$H]-collagen IV far above the degradation of $\beta_3$ negative CS-1 cells (which lack $\alpha_v\beta_3$). As shown in FIG. 9, treatment of these cells with Compound 19 significantly diminished the increased matrix degradation, consistent with the cells being unable to utilize MMP2, which is not bound to the integrin surface. Compound 19 did not, however, directly inhibit MMP2's proteolytic activity, as purified (active) enzyme in the absence cells was able to degrade [$^3$H]-collagen IV to a similar extent in the presence or absence of the Compound 19.

These results support the proposition that compounds of Formula (I) disrupt the ability of tumor cells to utilize MMP2 to degrade ECM proteins in a manner analogous to PEX. The compounds of Formula (I) do not interfere with the binding of $\alpha_v\beta_3$ to its classical RGD ligands nor do they function as a direct proteinase inhibitors.

The foregoing description and the Examples are to be taken as illustrative but not limiting. Still other variants within the spirit and scope of the present invention are possible and will readily present themselves to those skilled in the art.

What is claimed is:

1. A method of inhibiting the interaction of MMP2 with integrin $\alpha_v\beta_3$ in a host cell which comprises contacting the integrin with an interaction inhibiting amount of a compound represented by the formula:

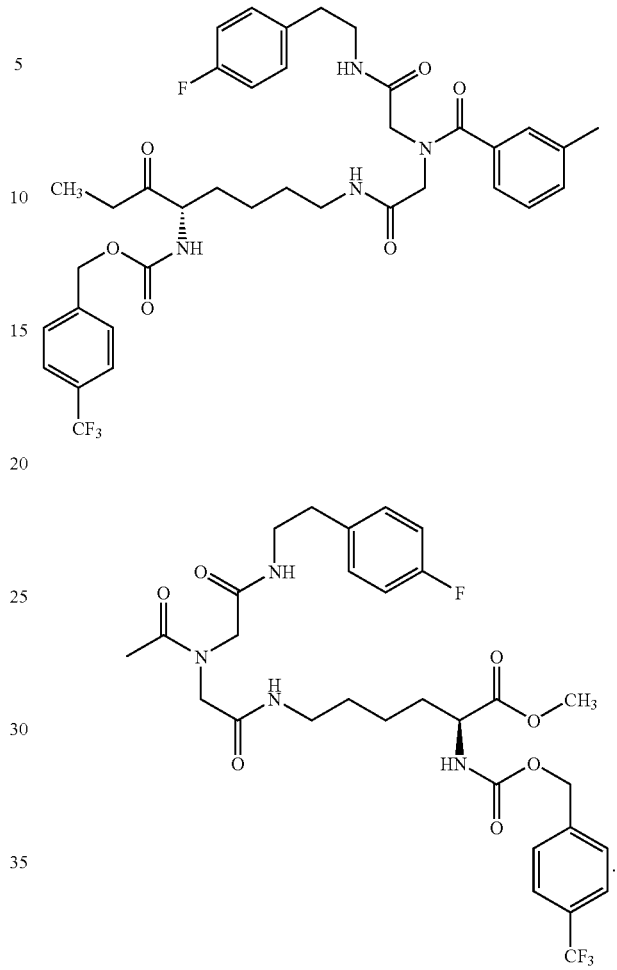

2. A method of inhibiting the interaction of MMP2 with integrin $\alpha_v\beta_3$ in a host cell which comprises contacting the integrin with an interaction inhibiting amount of a compound represented by the formula:

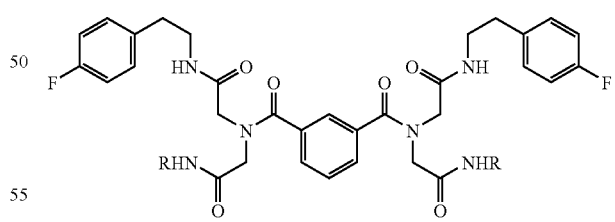

wherein R is selected from the group consisting of:

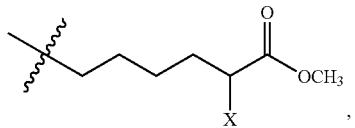

-continued
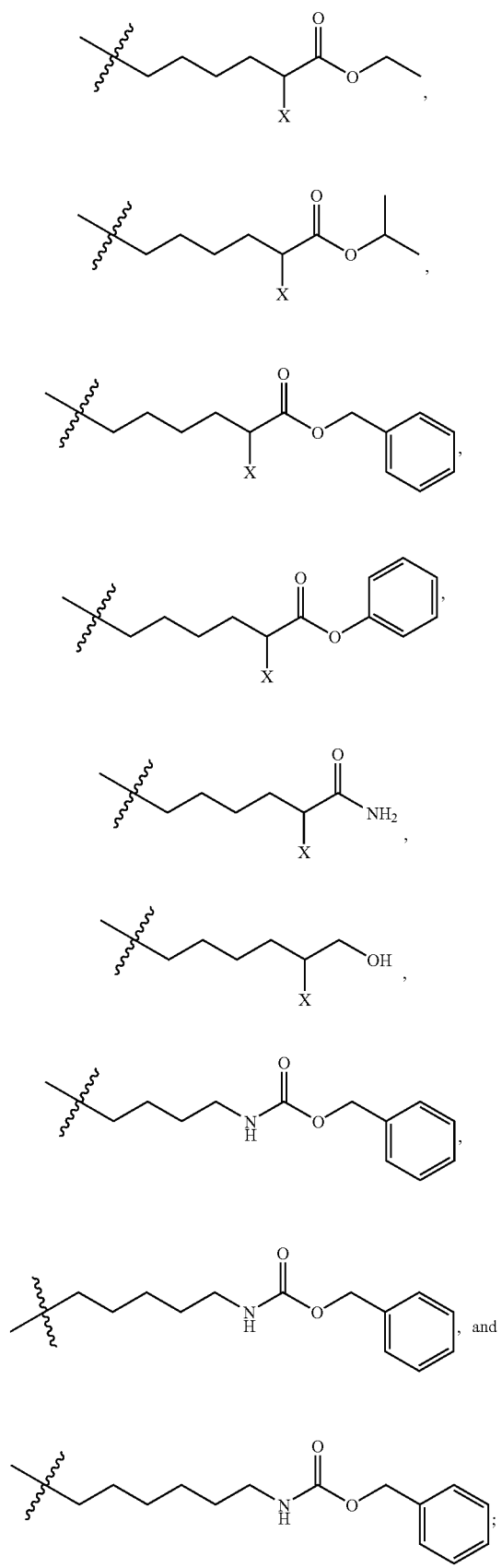
and X is selected from the group consisting of:
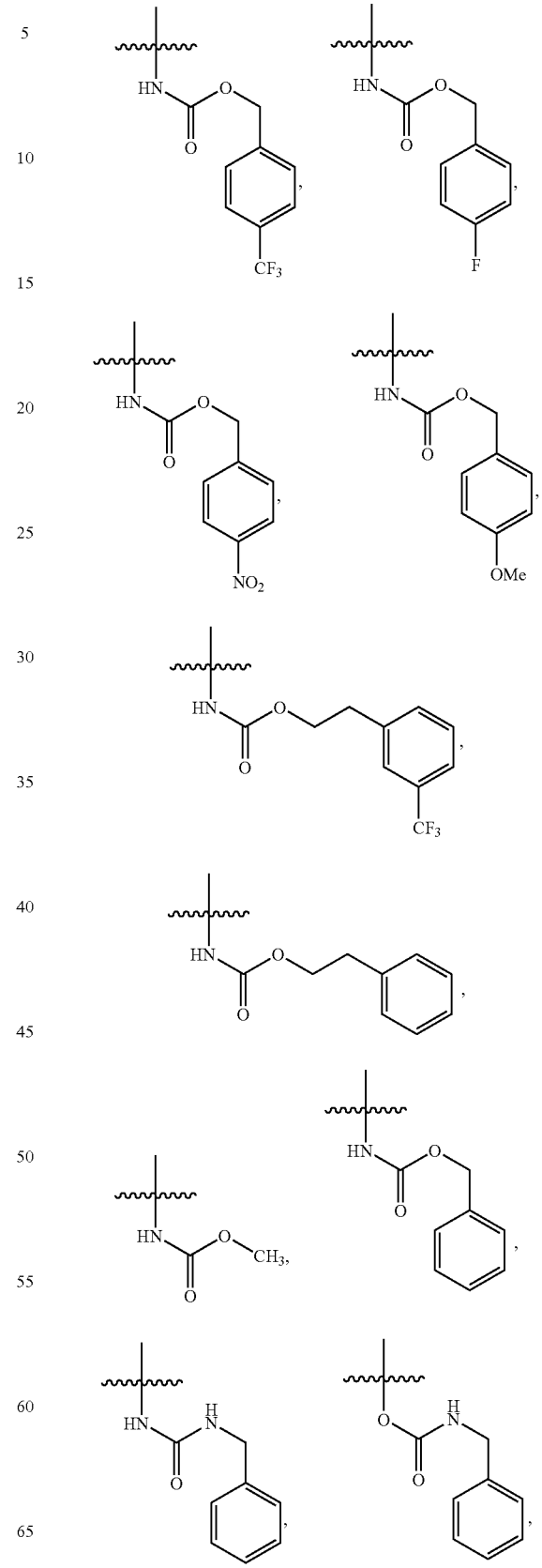

-continued
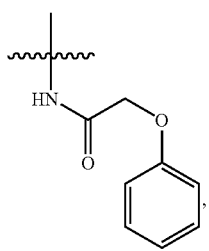 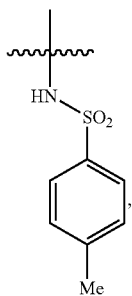 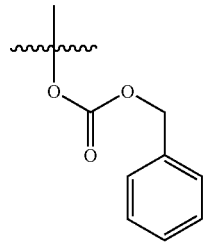, and 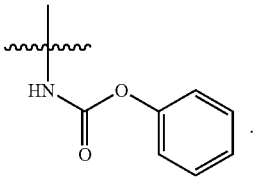.
* * * * *